US00PP34067P2

(12) United States Plant Patent
Caster et al.

(10) Patent No.: US PP34,067 P2
(45) Date of Patent: Mar. 29, 2022

(54) BLUEBERRY PLANT NAMED 'DRISBLUETWENTYFOUR'

(50) Latin Name: ***Vaccinium corymbosum* L.**
Varietal Denomination: DrisBlueTwentyFour

(71) Applicant: Driscoll's, Inc., Watsonville, CA (US)

(72) Inventors: Brian K. Caster, Watsonville, CA (US); Jennifer K. Izzo, Watsonville, CA (US); Bruce D. Mowrey, Watsonville, CA (US); Marta C. Baptista, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/179,253

(22) Filed: Feb. 18, 2021

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP19,503 | P3 | 11/2008 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Lyrene et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Rodriguez et al. |
| PP26,537 | P3 | 3/2016 | Caster et al. |
| PP26,643 | P3 | 4/2016 | Caster et al. |
| PP26,748 | P3 | 5/2016 | Rodriguez et al. |
| PP27,622 | P3 | 1/2017 | Caster et al. |
| PP28,933 | P2 | 2/2018 | Caster et al. |
| PP31,649 | P2 | 4/2020 | Caster et al. |
| PP31,650 | P2 | 4/2020 | Caster et al. |
| PP31,685 | P2 | 4/2020 | Mowrey et al. |
| PP31,698 | P2 | 4/2020 | Mowrey et al. |
| PP32,267 | P2 | 10/2020 | Caster et al. |
| PP32,744 | P3 | 1/2021 | Caster et al. |
| PP32,876 | P2 | 3/2021 | Mowrey et al. |

*Primary Examiner* — Anne Marie Grunberg
(74) *Attorney, Agent, or Firm* — Morrison & Foerster LLP

(57) ABSTRACT

A new and distinct variety of blueberry plant named 'DrisBlueTwentyFour', particularly selected for its sweet flavor, large fruit size, upright growth habit, and early season production, is disclosed.

8 Drawing Sheets

Latin name:
Botanical classification: *Vaccinium corymbosum* L.
Varietal denomination: The varietal denomination of the claimed variety of blueberry plant is 'DrisBlueTwentyFour'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueTwentyFour'.

Blueberry plant variety 'DrisBlueTwentyFour' was discovered in Santa Cruz County, Calif. in September of 2006 and originated from a cross between the proprietary female parent blueberry plant '136D 2' (unpatented) and the proprietary male parent blueberry plant '8B 4' (unpatented). The original seedling of the new variety was first asexually propagated via softwood cuttings in Monterey County, Calif. in July of 2007.

'DrisBlueTwentyFour' was subsequently asexually propagated via softwood cuttings and tissue culture and underwent further testing in Linn County, Oreg. for eight years (2011 to 2019). The present blueberry variety has been found to be stable and reproduce true to type through successive asexual propagations via softwood cuttings and tissue culture.

'DrisBlueTwentyFour' was selected for its sweet flavor, large fruit size, upright growth habit, and early season production.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are seven years old, unless otherwise specified.

DETAILED BOTANICAL DESCRIPTION

Figure 1:
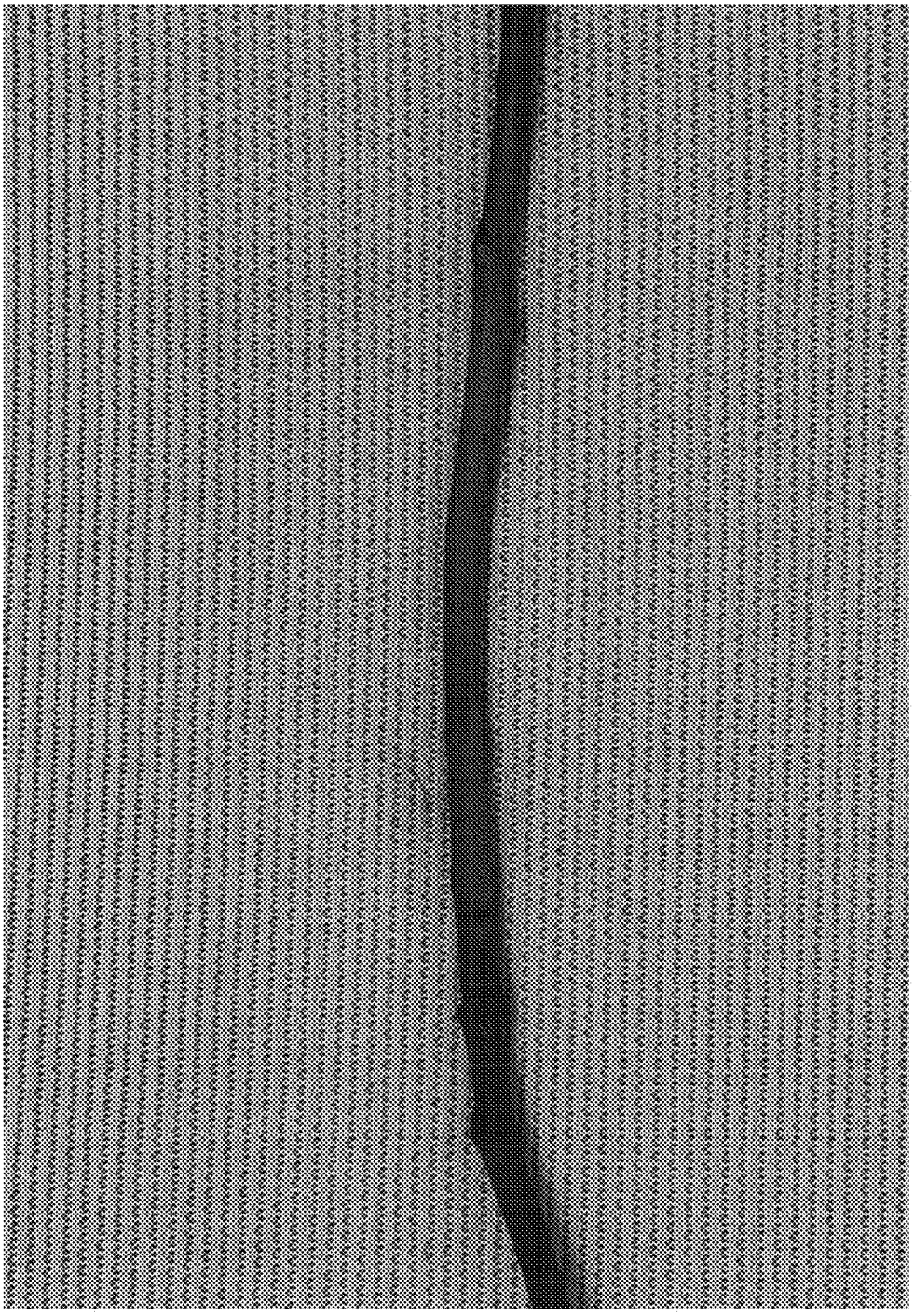
FIG. 1 illustrates a section of a cane of variety 'DrisBlueTwentyFour'.
Figure 2:
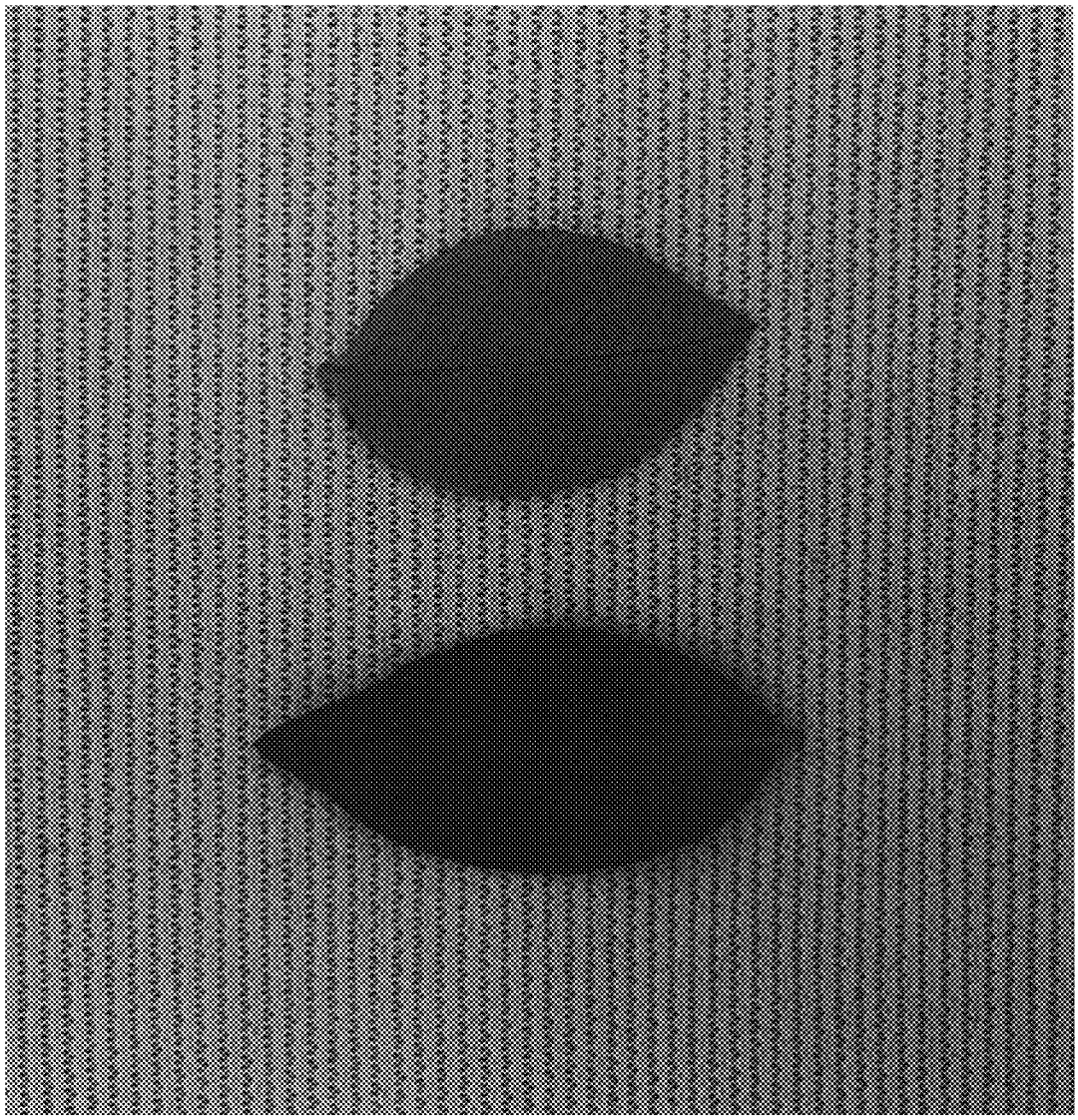
FIG. 2 illustrates leaves of variety 'DrisBlueTwentyFour'. The leaf on the left shows the upper leaf surface and the leaf on the right shows the lower leaf surface.
Figure 3:
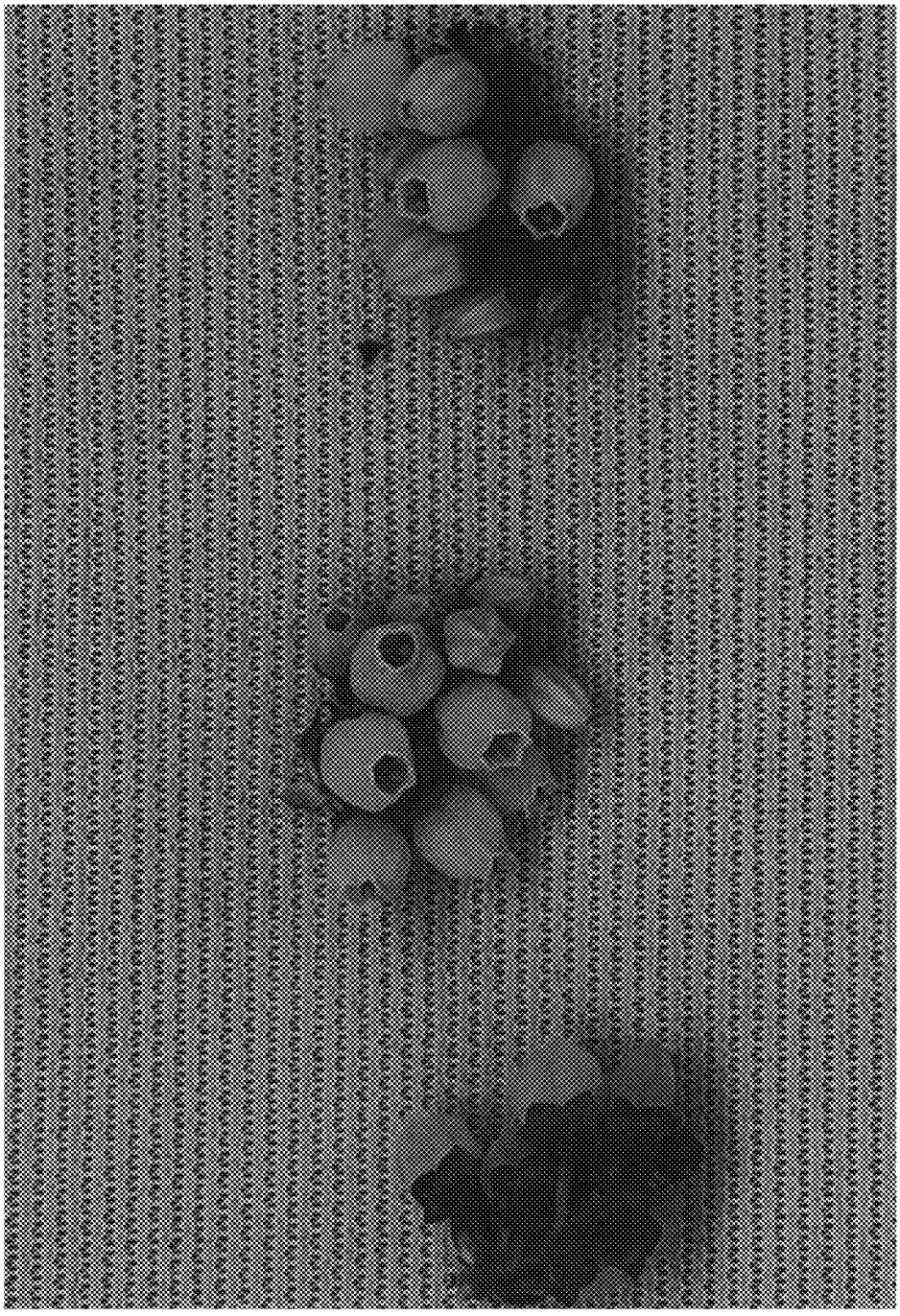
FIG. 3 illustrates clusters of flowers of variety 'DrisBlueTwentyFour'. The flower cluster on the left shows the bottom view, the flower cluster in the middle shows the top view, and the flower cluster on the right shows the side view.
Figure 4:
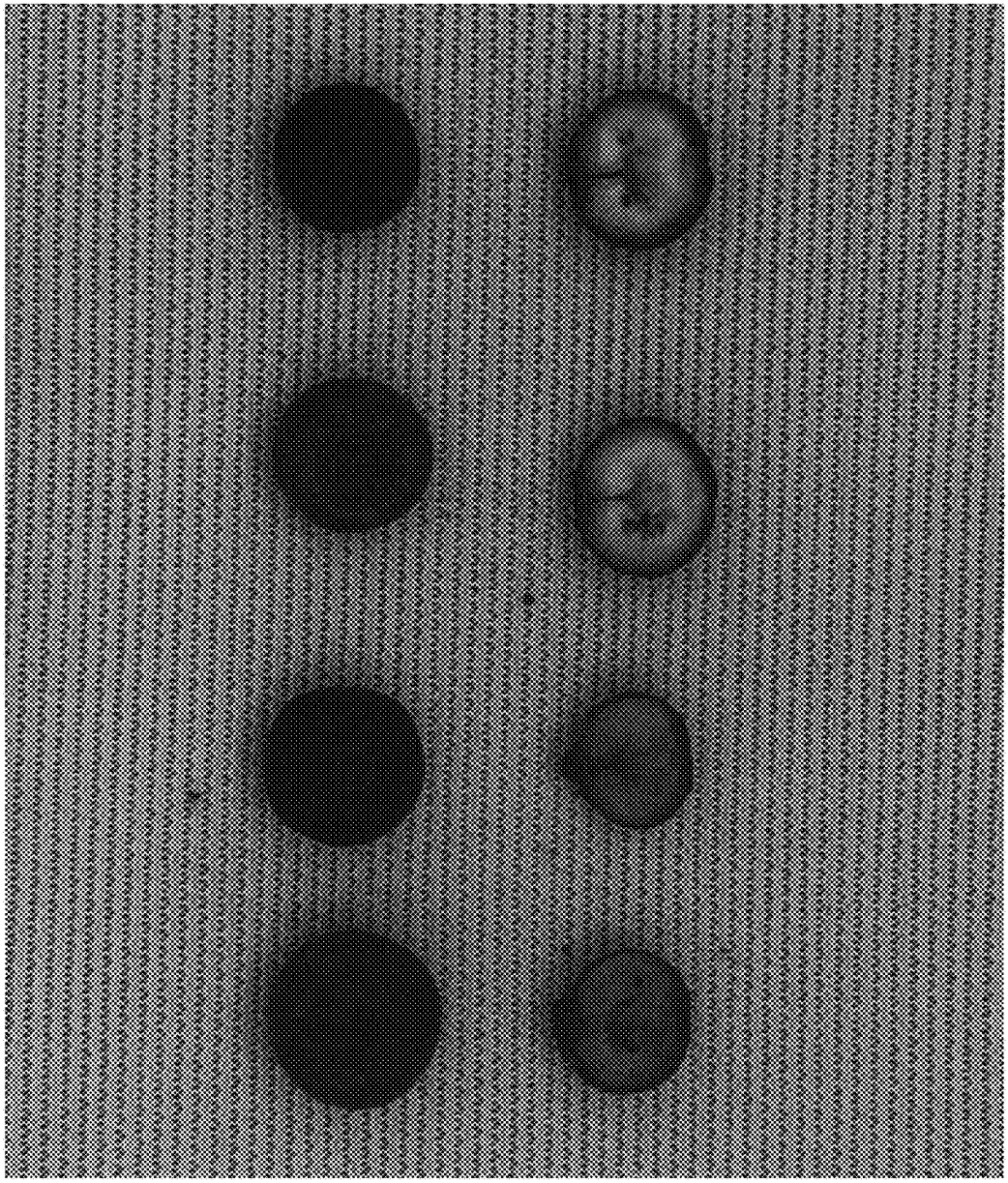
FIG. 4 illustrates top views of whole fruits (top row) and longitudinal sections (bottom row) of variety 'DrisBlueTwentyFour'. The two fruits on the top left show the bottom view (fruit-pedicel junction) of the whole fruit, whereas the two fruits on the top right show the top view (calyx basin) of the whole fruit. The first and third fruit of the top row have bloom on them, whereas the second and fourth fruit of the top row have bloom removed.
Figure 5:
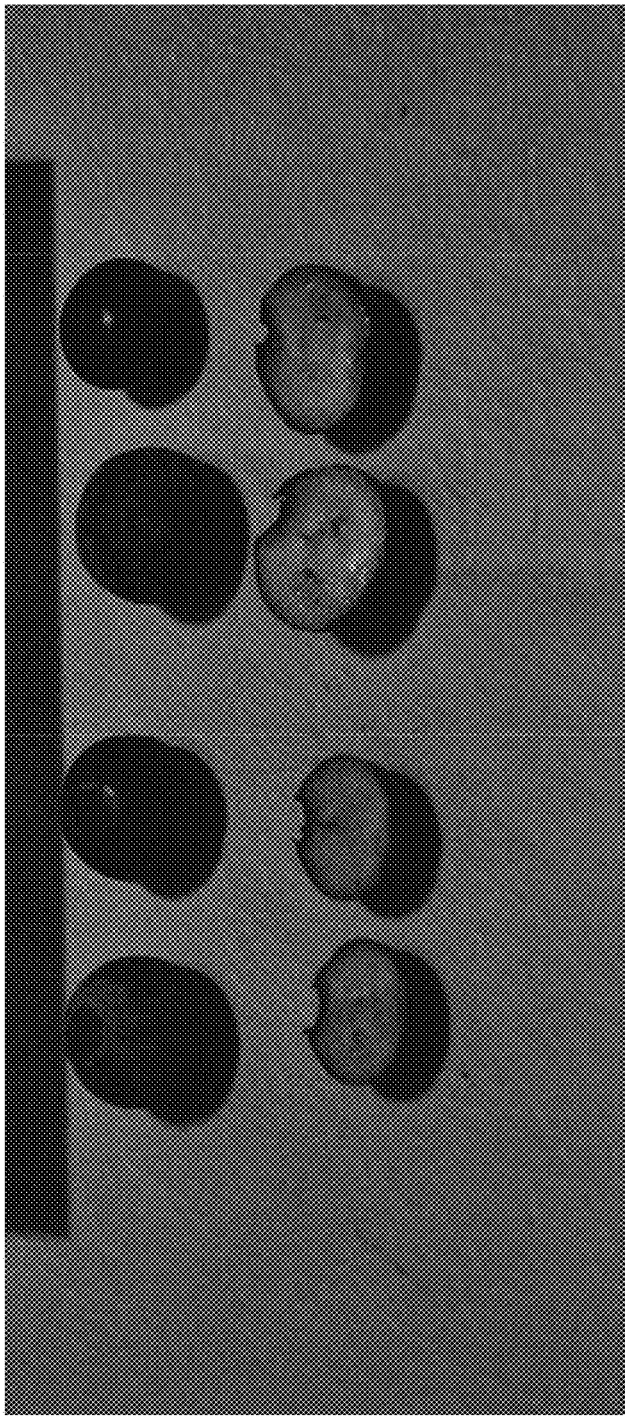
FIG. 5 illustrates side views of whole fruits (top row) and longitudinal sections (bottom row) of variety 'DrisBlueTwentyFour'.
Figure 6:
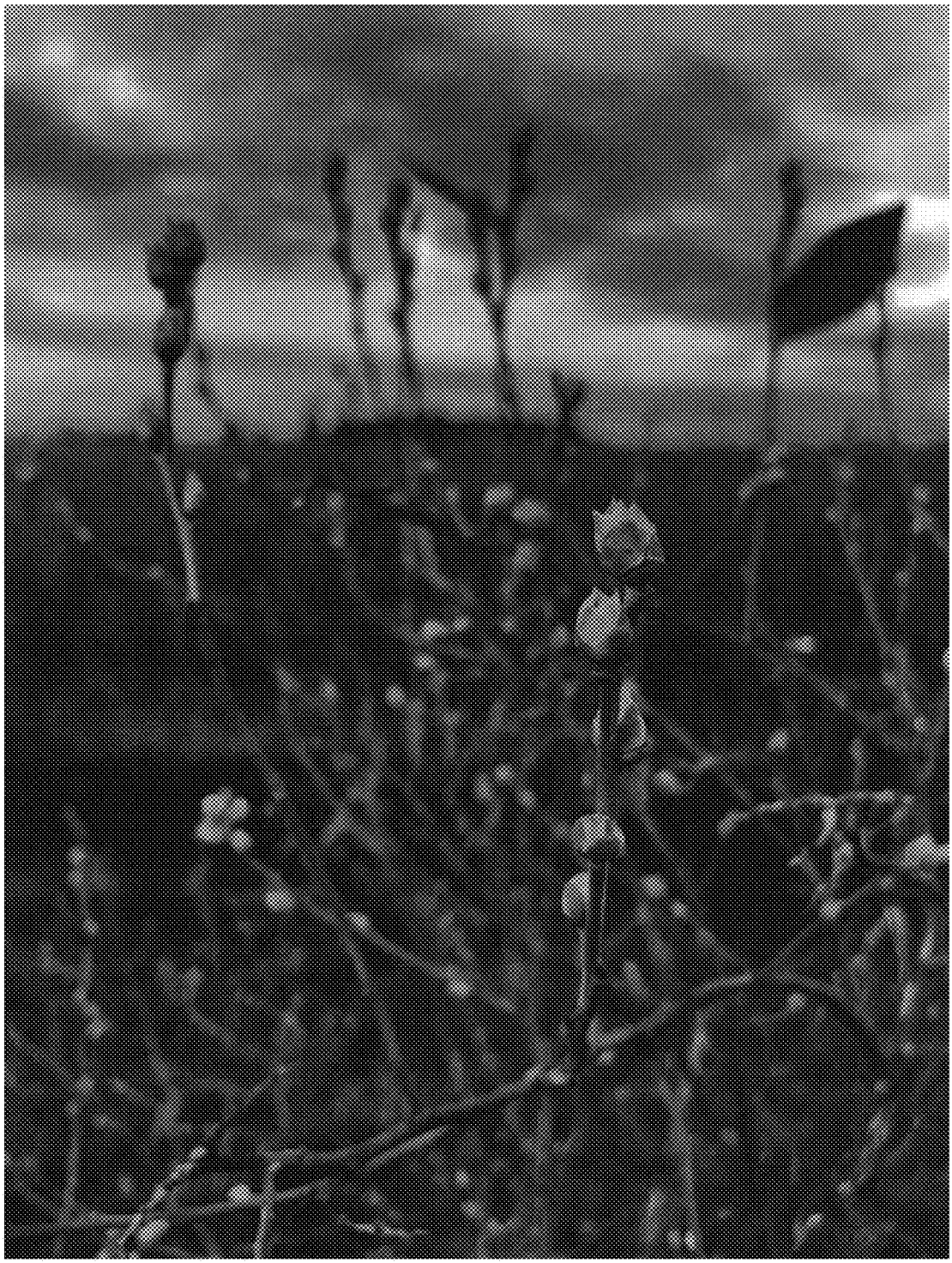
FIG. 6 illustrates buds on plants of variety 'DrisBlueTwentyFour'.
Figure 7:
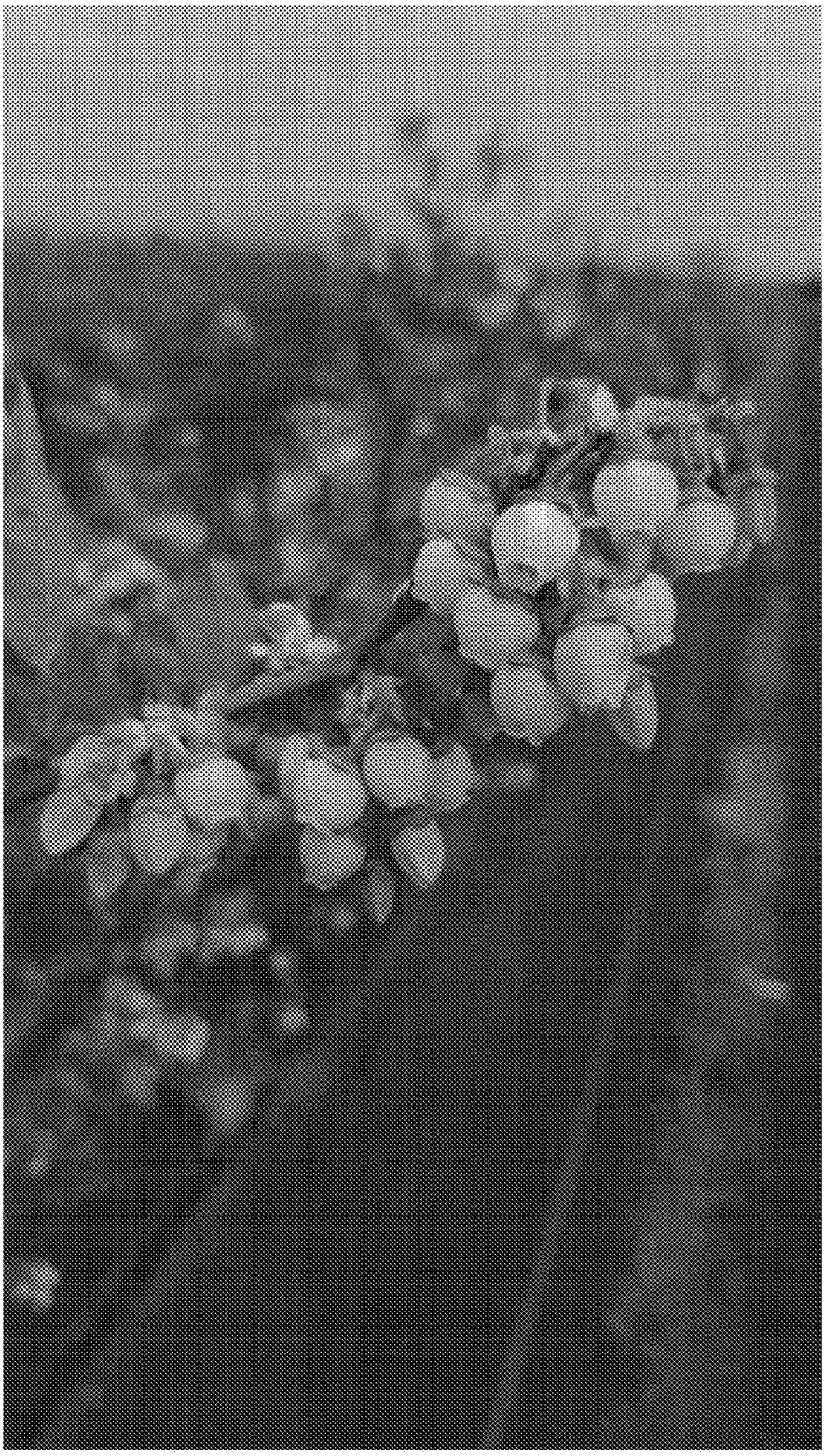
FIG. 7 illustrates flowers on plants of variety 'DrisBlueTwentyFour'.
Figure 8:
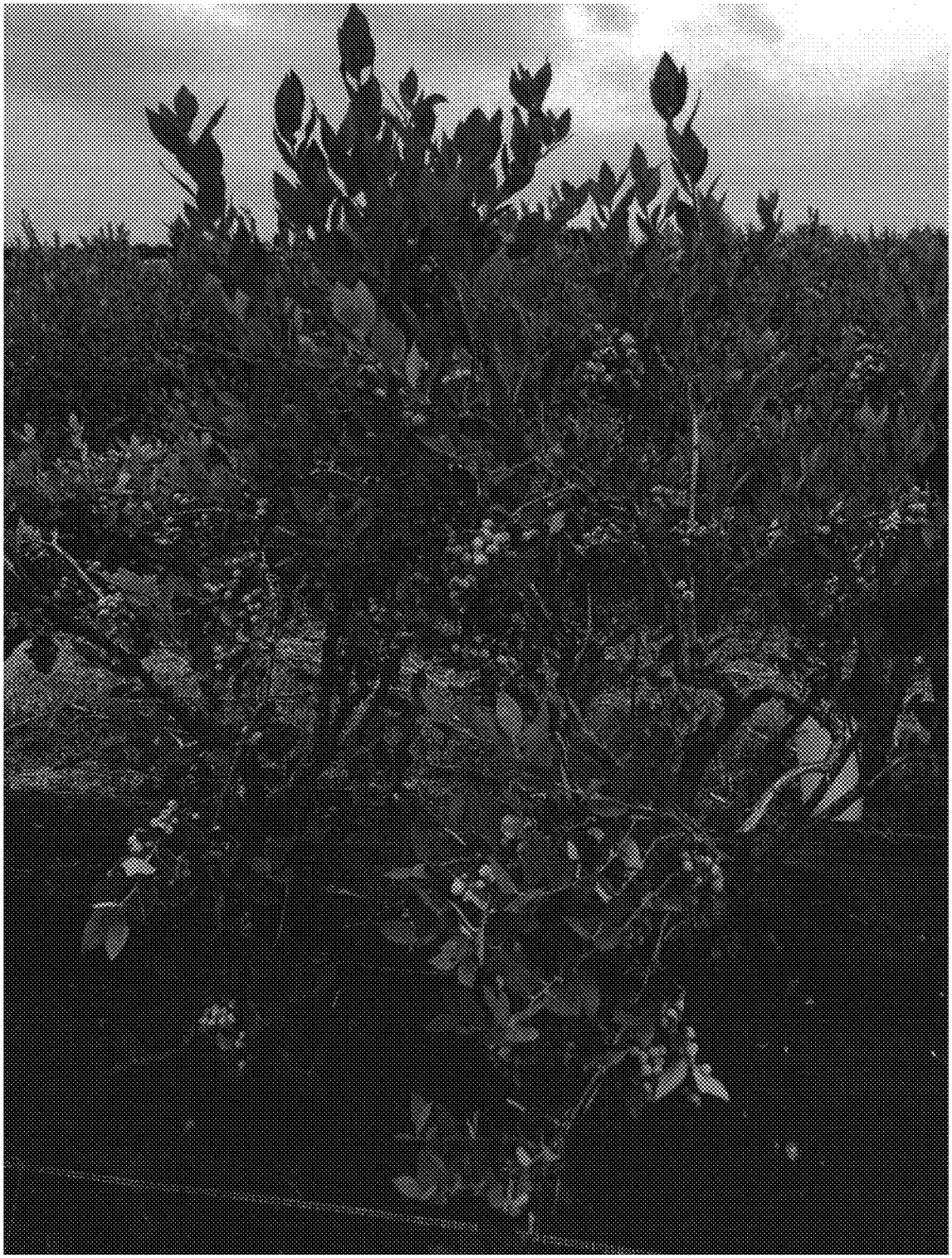
FIG. 8 illustrates whole plants of variety 'DrisBlueTwentyFour'.

The following description sets forth the distinctive characteristics of 'DrisBlueTwentyFour'. The data which define these characteristics is based on observations taken in Linn County, Oreg. from 2011 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlueTwentyFour' has not been observed under all possible environmental conditions. Unless noted otherwise, the botanical description of 'DrisBlueTwentyFour' was taken from plants that were seven years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family.*—Ericaceae.

*Botanical.*—*Vaccinium corymbosum* L.

*Common name.*—Blueberry.

*Variety name.*—'DrisBlueTwentyFour'.

Parentage:

*Female parent.*—The proprietary blueberry plant '136D 2' (unpatented).

*Male parent.*—The proprietary blueberry plant '8B 4' (unpatented).

Plant:

*Height.*—120.1 cm.

*Width.*—117.6 cm.

*Length/width ratio.*—1.0.

*Vigor.*—Medium.

*Growth habit.*—Upright.

*Chilling requirements.*—Minimum of 1,000 hours of chilling below 7° C. for proper vegetative and floral bud break.

*One-year-old canes* (*young canes*).—Length: 17 cm. Diameter at the base: 3 mm. Diameter at the tip: 2 mm. Internode length on the upper half: 11.7 mm. Color: RHS 176A (Greyish red).

*Five-year-old canes* (*mature canes*).—Length: 68 cm. Diameter at the base: 18 mm. Diameter at the tip: 11 mm. Color: RHS 199D (Dark greyish yellow).

Leaves:

*Length.*—65.0 mm.

*Width.*—36.0 mm.

*Length/width ratio.*—1.8.

*Shape.*—Ovate.

*Margin.*—Entire.

*Color on upper side.*—RHS 146A (Moderate olive green).

*Color of lower side.*—RHS N138C (Pale green).

*Leaf tip shape.*—Acute.

*Leaf base shape.*—Cuneate.

*Petiole.*—Length: 3.6 mm. Diameter: 1.47 mm. Color: RHS 143D (Moderate yellow-green).

Flowers:

*Flower length* (*excluding peduncle*).—10.92 mm.

*Flower diameter.*—8.82 mm.

*Flower length/width ratio.*—1.2.

*Flower bud.*—Length: 6.94 mm. Width: 4.14 mm. Number of flowers per bud: 8. Color with anthocyanin present: RHS 63B (Strong purplish red).

*Flower pedicel.*—Length: 5.41 mm. Diameter: 1.16 mm.

*Corolla*.—Shape: Urceolate. Color of corolla tube (with anthocyanin coloration): RHS 8C (Light greenish yellow). Ridges on corolla tube: Present. Petal width (ridge to ridge): 2.81 mm. Diameter of corolla aperture: 3.72 mm.

*Reproductive organs*.—Style length (including stigma): 8.74 mm.

*Flowering interval on one-year-old shoot*.—April to end of May.

Fruit:

*Length*.—16.56 mm.

*Diameter*.—20.60 mm.

*Length/width ratio*.—0.8.

*Weight*.—1.9 grams.

*Shape in longitudinal section*.—Round to oblate.

*Attitude of sepals*.—Erect to semi-erect.

*Type of sepals*.—50% incurving and 50% reflexed.

*Calyx basin*.—Diameter: 6.72 mm. Depth: 1.41 mm. Diameter/depth ratio: 4.8.

*Number of berries per cluster*.—8.70.

*Fruit cluster peduncle length*.—23.26 mm.

*Fruit cluster peduncle color*.—RHS 144C (Strong yellow-green).

*Diameter of fruit pedicel*.—1.15 mm.

*Color of unripe fruit*.—RHS 145A (Strong yellow green).

*Intensity of bloom*.—Medium.

*Color of fruit without bloom on mature fruit*.—RHS 103A (Greyish purplish blue).

*Fruit flesh color*.—RHS 192A (Pale yellow-green).

*Fruit firmness*.—Medium.

*Brix* (*soluble solids*).—13.9.

*Seed*.—Length: 1.20 mm. Width: 0.78 mm. Length/width ratio: 1.5. Seed color: RHS N167B (Brownish orange).

*Fruiting type*.—On one-year-old shoots only.

*Ripening interval on one-year-old shoot*.—Mid-June to mid-August.

*Yield*.—16,000 kg to 26,000 kg of fruit per hectare per season from 84-month old plants when grown at Albany, Oreg.

Resistance to abiotic stress, pests, and diseases:

*Botrytis fruit rot* (*botrytis cinerea*).—Moderately susceptible.

*Blueberry shock virus*.—Susceptible.

COMPARISONS TO PARENTAL AND REFERENCE BLUEBERRY VARIETIES

'DrisBlueTwentyFour' differs from the proprietary female parent '136D 2' (unpatented) in that 'DrisBlueTwentyFour' has a higher chilling requirement, better flavor, and larger fruit size when compared to female parent '136D 2'.

'DrisBlueTwentyFour' differs from the proprietary male parent '8B 4' (unpatented) in that it has a better overall appearance, better flavor, and larger fruit size when compared to male parent '8B 4'.

'DrisBlueTwentyFour' differs from the reference blueberry plant variety 'DrisBlueTen' (U.S. Plant Pat. No. 26,643) in that 'DrisBlueTwentyFour' has an upright growth habit, ovate leaf shape, medium anthocyanin coloration on corolla tube, and medium intensity of bloom on fruit, whereas 'DrisBlueTen' has a semi-upright to spreading growth habit, elliptic leaf shape, very weak or absent anthocyanin coloration on corolla tube, and strong intensity of bloom on fruit.

'DrisBlueTwentyFour' differs from the reference blueberry plant variety 'DrisBlueFourteen' (U.S. Plant Pat. No. 27,622) in that 'DrisBlueTwentyFour' has an upright growth habit, medium plant vigor, ovate leaf shape, and medium fruit firmness, whereas 'DrisBlueFourteen' has a semi-upright growth habit, strong plant vigor, elliptic leaf shape, and firm fruit.

What is claimed is:

1. A new and distinct variety of blueberry plant designated 'DrisBlueTwentyFour' as shown and described herein.

* * * * *